United States Patent
Levin (10) Patent No.: US 11,213,804 B2
(45) Date of Patent: Jan. 4, 2022

(54) DEHYDROGENATION CATALYSTS AND METHODS OF MAKING AND USING THE SAME

(71) Applicant: ExxonMobil Chemical Patents Inc., Baytown, TX (US)

(72) Inventor: Doron Levin, Highland Park, NJ (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 209 days.

(21) Appl. No.: 16/269,959

(22) Filed: Feb. 7, 2019

(65) Prior Publication Data

US 2019/0283002 A1 Sep. 19, 2019

Related U.S. Application Data

(60) Provisional application No. 62/644,753, filed on Mar. 19, 2018.

(51) Int. Cl.
*B01J 23/62* (2006.01)
*B01J 21/12* (2006.01)
(Continued)

(52) U.S. Cl.
CPC .............. *B01J 23/626* (2013.01); *B01J 21/12* (2013.01); *B01J 23/14* (2013.01); *B01J 37/0205* (2013.01);
(Continued)

(58) Field of Classification Search
CPC . B01J 21/04; B01J 21/066; B01J 21/08; B01J 21/12; B01J 21/16; B01J 21/18;
(Continued)

(56) References Cited

U.S. PATENT DOCUMENTS 4,048,245 A * 9/1977 Pollitzer .............. B01J 23/8966
585/434
6,037,513 A 3/2000 Chang et al.
(Continued)

FOREIGN PATENT DOCUMENTS

| CN | 104588007 | * | 5/2015 | .............. B01J 23/62 |
| WO | 2009/131769 | | 10/2009 | |
| WO | 2011/096998 | | 8/2011 | |
| WO | WO-2017179708 A1 * | 10/2017 | .......... B01J 37/0236 |

OTHER PUBLICATIONS

Ravanchi et al. to Mathematical modeling of platinum and chlorine distributions within Pt—Sn/Al2O3 catalyst prepared by impregnation, Scientia Irania C (2015), 22 (3), 981-991.*

*Primary Examiner* — Jun Li (57) ABSTRACT

Disclosed herein are methods of preparing dehydrogenation catalysts using non-halogen containing metal sources. The methods generally comprise the steps of providing a first solution comprising anions of a first metal selected from Group 14 of the Periodic Table of Elements, and impregnating an inorganic support with the first solution to obtain a first impregnated inorganic support, wherein the first solution has a pH value of less than the isoelectric point of the inorganic support. The dehydrogenation catalysts prepared in accordance with the methods of the present disclosure are typically free or substantially free of halogen species. Such catalysts may be particularly useful in the dehydrogenation of a feed comprising cyclohexane and/or methylcyclopentane.

19 Claims, 1 Drawing Sheet

(51) Int. Cl.
*B01J 23/14* (2006.01)
*B01J 37/02* (2006.01)
*B01J 37/08* (2006.01)
*C07C 5/32* (2006.01)
*B01J 37/34* (2006.01)

(52) U.S. Cl.
CPC ........... *B01J 37/0236* (2013.01); *B01J 37/08* (2013.01); *B01J 37/346* (2013.01); *C07C 5/325* (2013.01)

(58) Field of Classification Search
CPC .... B01J 21/185; B01J 23/626; B01J 37/0205; C07C 5/325; C07C 5/367; C07C 2523/14; C07C 2523/62
See application file for complete search history.

(56) References Cited

U.S. PATENT DOCUMENTS

| | | | |
|---|---|---|---|
| 7,375,049 B2 * | 5/2008 | Hayes | B01J 23/626 502/185 |
| 7,579,511 B1 | 8/2009 | Dakka et al. | |
| 9,469,580 B2 | 10/2016 | Chen et al. | |
| 9,580,368 B2 | 2/2017 | Chen et al. | |
| 9,782,754 B2 * | 10/2017 | Al-Zahrani | B01J 23/36 |
| 2005/0009694 A1 * | 1/2005 | Watts | B01J 23/40 502/304 |
| 2010/0249479 A1 * | 9/2010 | Berg-Slot | C07C 4/18 585/489 |
| 2019/0201874 A1 * | 7/2019 | Segawa | B01J 35/002 |

\* cited by examiner

ововgone,

DEHYDROGENATION CATALYSTS AND METHODS OF MAKING AND USING THE SAME

CROSS-REFERENCE TO RELATED APPLICATION

This is a utility patent application claiming priority to provisional patent application U.S. Ser. No. 62/644,753 filed Mar. 19, 2018, which is incorporated herein by reference.

FIELD

The present invention relates to a dehydrogenation catalyst, methods of making the same, and processes using the same for dehydrogenating saturated cyclic hydrocarbons such as cyclohexane and/or methylcyclopentane.

BACKGROUND

Phenol and cyclohexanone are important compounds in the chemical industry and are useful in, for example, production of phenolic resins, bisphenol A, ε-caprolactam, adipic acid, and plasticizers.

Currently, a common route for the production of phenol is the Hock process. This is a three-step process in which the first step involves alkylation of benzene with propylene to produce cumene, followed by oxidation of cumene to the corresponding hydroperoxide, and then cleavage of the hydroperoxide to produce equimolar amounts of phenol and acetone. The separated phenol product can then be converted to cyclohexanone by a step of hydrogenation.

It is known from, e.g., U.S. Pat. No. 6,037,513, that cyclohexylbenzene can be produced by contacting benzene with hydrogen in the presence of a bifunctional catalyst comprising a molecular sieve of the MCM-22 type and at least one hydrogenation metal selected from palladium, ruthenium, nickel, cobalt, and mixtures thereof. This reference also discloses that the resultant cyclohexylbenzene can be oxidized to the corresponding hydroperoxide, which can then be cleaved to produce a cleavage mixture of phenol and cyclohexanone, which, in turn, can be separated to obtain pure, substantially equimolar phenol and cyclohexanone products.

One disadvantage of this cyclohexylbenzene-based process is that it produces impurities such as cyclohexane and methylcyclopentane. These impurities represent loss of valuable benzene feed. Moreover, unless removed, these impurities will tend to build up in the system, thereby displacing benzene and increasing the production of undesirable by-products. Thus, a significant problem facing the commercial application of cyclohexylbenzene as a phenol precursor is removing the cyclohexane and methylcyclopentane impurities.

It is known from, e.g., U.S. Pat. No. 7,579,511, WO2009/131769, and WO2011/096998 that the concentration of these impurities can be reduced via dehydrogenation in the presence of a dehydrogenation catalyst.

More recently, it was discovered that catalyst comprising a metal selected from Group 14 of the Periodic Table of Elements can be used to dehydrogenate cyclohexane and/or methylcyclopentane. This process is disclosed, for example, in U.S. Pat. Nos. 9,580,368 and 9,469,580. It is known, e.g., from the '368 and '580 patents, that the Group 14 metal(s) can be deposited on the support surface of the dehydrogenation catalyst by impregnation. Metal halides, e.g., $SnCl_2$, are a convenient source of the Group 14 metal(s) in view of their low cost and high solubility in an aqueous solution. Additionally, the cationic nature of the metal ion in said metal halides allows for good dispersion of the metal over a silica source.

However, the use of a metal halide as the metal source also results in the presence of halogens in various forms, e.g., halides, particularly chlorides, on the finished catalyst, e.g., resulting in a chlorine concentration of greater than about 0.10 wt % by weight of the finished catalyst. Although the halogen content of the finished catalyst can be reduced during activation, the resulting release of halogen species, e.g., chlorides and HCl formed during activation, into the reactor system is undesirable for a variety of reasons. For example, in such aspects the metallurgy of the reactor and downstream equipment needs to be suitable to avoid halogen, e.g., chloride/HCl, induced corrosion, thereby limiting the ability to use carbon steel. Additionally, it is typically desirable to remove released halogen species, e.g., HCl, from the system, either via purging, which results in a loss of production, or via adsorption with additional equipment, which increases the cost of the dehydrogenation. Accordingly, it would be advantageous to provide a dehydrogenation catalyst having a low halogen content prior to or in lieu of activation.

As an alternative to metal halides, an anionic species can be used as the source of the dehydrogenation metal(s), e.g., potassium stannate. The use of such an anionic species avoids the presence of chlorides in the finished catalyst. However, in using an anionic species, a combination of the dehydrogenation metal(s) being present in anionic form and the high pH of the impregnation solution results in poor dispersion of the metal(s) on the negatively charged support surface.

Thus, in order to solve the above-mentioned problems, there is a need to provide dehydrogenation catalyst compositions that are free of halogen species and that exhibit uniform distribution of the dehydrogenation metal(s) on the support. There is also a need to provide methods of making such dehydrogenation catalysts and dehydrogenation processes using the same.

SUMMARY

A first aspect of the present disclosure relates to a method of preparing a dehydrogenation catalyst, the method comprising the steps of: a) providing a first solution containing anions of a first metal, wherein the first metal is selected from Group 14 of the Periodic Table of Elements, preferably tin; and b) impregnating an inorganic support with the first solution to obtain a first impregnated inorganic support, wherein the first solution has a pH value of less than the isoelectric point of the inorganic support, for example less than about 6.5, such as from about 1 to about 6. Often, the pH value of the first solution of step a) is adjusted via addition an acid, preferably a carboxylic acid. Typically, the first solution is substantially free of halogen species, e.g., chlorine. Typically, the catalyst preparation method of the present disclosure may further comprise the steps of c) providing a second solution comprising cations of a second metal, wherein the second metal is selected from Groups 6-10 of the Periodic Table of Elements, preferably palladium and/or palladium; and d) impregnating the first impregnated inorganic support with the second solution, wherein the second solution has a pH value of greater than the isoelectric point of the inorganic support, for example, greater than about 6.5, such as from about 8 to about 14.

A second aspect of the present disclosure relates to a dehydrogenation catalyst composition comprising (i) anions of a first metal, wherein the first metal is selected from Group 14 of the Periodic Table of Elements, preferably tin; and (ii) optionally, cations of a second metal, wherein the second metal is selected from Groups 6-10 of the Periodic Table of Elements, preferably palladium and/or palladium, wherein the anions of the first metal, and optionally the cations of the second metal, are deposited on a silica-containing support. The dehydrogenation catalyst composition is generally subjected to a calcination step and/or activation step prior to being used in a dehydrogenation reaction, generally resulting in a composition comprising at least the first metal in oxide and/or elemental form. In any embodiment, the dehydrogenation catalyst composition can be free or substantially free of halogen species.

A third aspect of the present disclosure relates to a dehydrogenation process employing a dehydrogenation catalyst of the present disclosure. A hydrogenation feed suitable for use in the dehydrogenation process of the present disclosure can be obtained by a) contacting benzene and hydrogen with a hydroalkylation catalyst under hydroalkylation conditions effective to convert benzene to cyclohexylbenzene and cyclohexane; and b) separating at least a portion of the cyclohexane from step a) to form the dehydrogenation feed.

DETAILED DESCRIPTION

As discussed above, the present disclosure is directed at least in part towards methods for preparing a dehydrogenation catalyst. The methods of the present disclosure have at least one or more of the following advantages. First, by utilizing halogen-free metal sources, e.g., potassium stannate as opposed to stannous chloride, the resulting dehydrogenation catalyst is free or substantially free of halogen species, e.g., chlorine. Accordingly, typical problems arising from activation of a conventional dehydrogenation catalyst, e.g., corrosion of process equipment and/or added costs of processing steps to remove halogen, may be reduced or eliminated through the methods described herein. Second, by utilizing the methods described herein, the metal(s) can be uniformly distributed on the support surface. Third, the distribution, and resulting dispersion, of the metal(s) can be controlled by the methods described herein, allowing for control of catalytic performance, e.g., selectivity and catalyst deactivation rate.

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are performed in the order as listed.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenation metal" include embodiments where one, two, or more different types of the hydrogenation metals are used, unless specified to the contrary or the context clearly indicates that only one type of the hydrogenation metal is used.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. All ranges expressed herein should include both end points as two specific embodiments unless specified or indicated to the contrary.

Unless otherwise specified, as used herein, a composition that is "substantially free" of a component means that the component is present at a concentration of less than about 0.1 wt % by weight of the composition. For example, as used herein, a composition, e.g., a catalyst or solution, that is "substantially free of halogen species" means that the halogen content, e.g., chlorine content, in the composition is less than about 0.10 wt %, 0.095 wt %, 0.090 wt %, 0.085 wt %, 0.08 wt %, 0.075 wt %, 0.07 wt %, 0.065 wt %, 0.06 wt %, 0.055 wt %, 0.05 wt %, 0.045 wt %, 0.04 wt %, 0.035 wt %, 0.03 wt %, 0.025 wt %, 0.02 wt %, 0.015 wt %, 0.01 wt %, 0.005 wt %, or about 0.001 wt % based on the weight of the composition, such as about 0 wt % based on the weight of the composition.

As used herein, the terms "anion," "anionic form," and "anionic species" with respect to a metal interchangeably refer to negatively charged atoms of the metal or negatively charged groups of atoms containing the metal. As used herein, the term "stannate" refers to a salt of stannic acid, for example, a salt containing units of $SnO_4^{4-}$, $SnO_2^{2-}$, or $SnO_3^{2-}$. As used herein, the term "stannate ion" refers to the anionic group of a salt of stannic acid, e.g., $SnO_4^{4-}$, $SnO_2^{2-}$, or $SnO_3^{2-}$. As used herein, the term "stannide" refers to a compound containing $Sn_x^{y-}$ ions, where x is an integer ranging from 1 to 12, and y is an integer ranging from 1 to 7, for example, $Sn^{4-}$, $Sn_4^{4-}$, $Sn^{2-}$, $Sn_4^{2-}$, $Sn_5^{2-}$, $Sn_8^{4-}$, $Sn_9^{4-}$, $Sn_9^{3-}$, or $Sn_{12}^{7-}$.

As used herein, the hydrogen chemisorption value (hcv) of a particular catalyst is a measure of metal dispersion on the catalyst and is defined as:

$$hcv(H/Pt) = \frac{\text{amount of hydrogen sorbed by the catalyst in moles}}{\text{amount of dehydrogenation metal contained in the catalyst in moles}}.$$

The hydrogen chemisorption values referred to herein are measured using a Micromeritics ASAP 2020 chemisorption analyzer as follows. Approximately 1.0 gram of catalyst are placed in the Micrometrics device. Under flowing helium, the catalyst is ramped from ambient (18° C.) to 250° C. at a rate of 10° C. per minute and held for 60 minutes. After 60 minutes, the catalyst is held at 250° C. in flowing hydrogen for a further 60 minutes. After this step, the sample is placed under vacuum at 250° C. for 60 minutes. After 60 minutes of vacuum, the sample is cooled to 35° C. at 20° C. per minute and held for 5 minutes. The hydrogen isotherm is collected in increments at 35° C. between 1 and 750 mm Hg. Extrapolation of the linear portion of this curve to zero pressure gives the total (i.e., combined) adsorption uptake.

As used herein, the "isoelectric point" (IEP) refers to that state where the surface of particles in a medium is not charged, which corresponds to a pH value for a particular material, for example an inorganic oxide support, in a particular medium, for example water. Unless otherwise specified, the IEP values referred to herein are determined from the measurements of zeta-potential using a Matec ESA 9800 electrokinetic instrument available from Matec Applied Science, Northboro, Mass. Zeta-potentials are calculated from measurements of an ultrasonic signal originating from distortion of the colloidal particle's double in a high frequency ac field. Conversion of the ultrasonic signal into a zeta-potential value factors in particle size, particle density, and volume fraction of the suspended solid.

As used herein, the generic term "dicylcohexylbenzene" includes, in the aggregate, 1,2-dicyclohexylbenzene, 1,3-dicylohexylbenzene, and 1,4-dicyclohexylbenzene, unless clearly specified to mean only one or two thereof. The term cyclohexylbenzene, when used in the singular form, means mono substituted cyclohexylbenzene.

In the present disclosure, the composition of catalysts are expressed on the basis of the dry components. To the extent that the catalyst materials may entrain water to different degrees, such water is not considered in its composition. While the catalyst materials may be processed and/or used with a small quantity of water contained therein, it is preferred that the activated catalyst is dry (e.g., having a water content of at most 5.0 wt %, or at most 3.0 wt %, or at most 1.0 wt %, or at most 0.5 wt %, or at most 0.1 wt %) when put into use in a dehydrogenation process according to the present disclosure. In the present disclosure, the quantities of the metals in the catalysts thereof are expressed on the basis of elemental metal, regardless of the oxidation state thereof, even though they may be present in the materials at issue in the form of, e.g., in whole or in part, salts, oxides, complexes, and elemental metals. For example, a catalyst composition made with 1.9 grams of tin chloride salt (1.0 gram of tin) and 22.29 grams of tetraamine platinum hydroxide solution (4.486 wt % Pt) that is supported on 98 grams of silicon dioxide contains 1.0 wt % of tin and 1.0 wt % Pt, based upon the total weight of the catalyst composition in dry components. Also, the composition of the catalyst is expressed in terms of the final composition of the activated catalyst prepared therefrom. One having ordinary skill in the art of catalyst preparation can batch the starting materials, such as salts, solutions, oxides, and the like, to achieve a final target chemical composition of the activated catalyst. For example, in the present disclosure, a catalyst comprising 1.0 wt % of Pt, 1.0 wt % Sn, and 98.0 wt % of silica means a catalyst comprises the desired amount of starting materials such as one or more of $PtO_2$, Pt, $SnO_2$, SnO and the like, that upon activation, would be converted into a final catalyst comprising platinum, tin, and silica in the above amounts.

As used herein, the numbering scheme for the Periodic Table Element Groups disclosed herein is on the inside cover of *Hawley's Condensed Chemical Dictionary* (14$^{th}$ Edition), by Richard J. Lewis.

The term "MCM-22 type material" (or "material of the MCM-22 type" or "molecular sieve of the MCM-22 type" or "MCM-22 type zeolite"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one, or more than one, unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in WO 97/17290), MCM-36 (described in U.S. Pat. No. 5,250,277), MCM-49 (described in U.S. Pat. No. 5,236,575), and MCM-56 (described in U.S. Pat. No. 5,362,697). Other molecular sieves, such as UZM-8 (described in U.S. Pat. No. 6,756,030), may be used alone or together with the MCM-22 type molecular sieves as well for the purpose of the present disclosure. Desirably, the molecular sieve is selected from (a) MCM-49; (b) MCM-56; and (c) isotypes of MCM-49 and MCM-56, such as ITQ-2.

The dehydrogenation catalysts disclosed herein are in solid state under use conditions. The catalyst material in use may exhibit multiple or a single geometry and size. Thus, the catalyst may manifest itself as pellets, powders, or monolithic bodies. For the convenience of description herein, these different solid manifestations are connectively called "particles," regardless of their actual sizes, which may range from nanoscopic to macroscopic scales. For the convenience of description, the term "particle" is also used interchangeably with the term "pellet" herein. For each particle or pellet, there is a hypothetical three-dimensional rectangular cuboid capable of containing the particle having three dimensions a, b, and c, where a≥b≥c, with the smallest possible volume. The longest dimension of the rectangular cuboid, a, is called the longest axis of the particle.

Catalyst Preparation Methods

The present disclosure provides methods of preparing dehydrogenation catalysts that are free or substantially free of halogen species, e.g., chlorine, by using halogen-free metal sources.

The dehydrogenation catalysts of the present disclosure typically comprise (i) an inorganic support; (ii) a first metal selected from Group 14 of the Periodic Table of Elements; optionally (iii) a second metal selected from Groups 6-10 of the Periodic Table of Elements; and optionally (iv) a third metal selected from Groups 1 and 2 of the Periodic Table of Elements. For example, the dehydrogenation catalyst may comprise both the first metal and the second metal, but is essentially free of the third metal.

Typically, the catalyst preparation methods described herein comprise the steps of: a) providing a first solution containing anions of a first metal, wherein the first metal is selected from Group 14 of the Periodic Table of Elements, preferably tin; and b) impregnating an inorganic support with the first solution to obtain a first impregnated inorganic support, wherein the first solution has a pH value of less than the isoelectric point of the inorganic support.

The first solution can be prepared by dissolving a source of the first metal, or a precursor thereof, in a solution carrier, e.g., water. Optionally, an organic dispersant may be added to assist in uniform application of the first metal component to the support. Suitable organic dispersants include amino alcohols and amino acids, such as arginine. For example, the organic dispersant may be present in the solution composition in an amount between 1.0 wt % and 20 wt % of the solution composition.

Preferably, the first metal is tin. Generally, useful sources or precursors of the first metal are free or substantially free of halogen species, e.g., chlorine. Preferred sources or precursors of the first metal contain the first metal in anionic form. For example, preferred sources of tin include, but are not limited to, stannates, e.g., $K_2SnO_3$, $K_4SnO_4$, or $Na_2SnO_3$, and stannides, e.g., $K_4Sn_9$, $Mg_2Sn$, $Nb_3Sn$, $BaSn$, or $Na_7Sn_{12}$.

The inorganic support may comprise one or more of silica, alumina, a silicate, an aluminosilicate, zirconia, carbon, or carbon nanotubes. Alternatively, the support may comprise an inorganic oxide such as one or more of silicon dioxide, titanium dioxide, and zirconium dioxide. Preferably, the support is a silicon-containing support and comprises less than about 0.5 wt % of alumina. More preferably, the support is free or substantially free of alumina. The support may or may not comprise a binder. Impurities that can be present in the catalyst support are, for example, sodium salts such as sodium silicate, which can be present from anywhere from 0.01 wt % to 2 wt %. Suitable silica supports are described in, for example, WO 2007/084440 A1 and is hereby incorporated by reference for this purpose. In any embodiment, the inorganic oxide and the optional binder can be composited and formed into pellets by, e.g., extrusion, which is then impregnated by the one or more solutions as described herein.

Suitable silica supports typically have pore volumes and median pore diameters determined by the method of mercury intrusion porosimetry described by ASTM D4284. The silica support may have surface areas as measured by ASTM D3663. The pore volumes may be in the range from about 0.2 cc/gram to about 3.0 cc/gram. The median pore diameters are in the range from about 10 angstroms to about 2000 angstroms, or from 20 angstroms to 500 angstroms; and the surface areas ($m^2$/gram) are in the range from 10 to 1000 $m^2$/gram, or from 20 to 500 $m^2$/gram. The support may or may not comprise a binder.

Preferred silica supports may have an IEP of about 1 to about 6, or about 1 to about 4, for example, from about 1.7 to about 3.5, as described in Marek Kosmulski, "*Chemical Properties of Material Surfaces*", Marcel Dekker, 2001. The actual value of the IEP will depend on various factors such as the actual composition of the silica support.

Generally, the first solution has a pH value of less than the IEP of the inorganic support. For example, the first solution may preferably have a pH value of less than about 6.5, or less than about 6.0, or less than about 5.5, or less than about 5.0, or less than about 4.5, or less than about 3.0, or less than about 2.5, for example from about 0.1 to about 6.5, or from about 0.5 to about 6.5, or from about 0.5 to about 6.0, or from about 1.0 to about 6.0, or from about 1.0 to about 4.0, or from about 1.0 to about 3.5, or from about 1.0 to about 2.5, or from about 1.5 to about 2.5, or from about 2.0 to about 2.5.

Typically, utilizing sources or precursors of the first metal containing the first metal in anionic form as compared to cationic form results in a solution having a higher pH. For example, an aqueous solution prepared from potassium stannate may have a pH value of about 11. Thus, often, the pH value of the first solution may be adjusted via addition of an acid, preferably a halogen-free acid, for example, an organic acid, such as but not limited to a carboxylic acid. Useful carboxylic acids comprise, but are not limited to, citric acid, acetic acid, oxalic acid, gluconic acid, glyoxylic acid, glycolic acid, lactic acid, valeric acid and adipic aid. The amount of the carboxylic acid added to the first solution is typically varied depending on the inorganic support selected. For example, typically the carboxylic acid can be added in an amount such that the molar ratio of the carboxylic acid to the first metal element in solution ranges from about 1 to about 15, or from about 2 to about 15, or from about 2 to about 10, or from about 3 to about 8.

The impregnation of the inorganic support with the first solution to obtain a first impregnated support can generally be conducted at a temperature of less than about 100° C., for example, from about 20 to about 25° C., for a time period of at least about 0.1, 0.2, 0.5, 0.8, 1.0, 1.5, 2.0, 3.0, 4.0, 5.0, 6.0, 7.0, 8.0, 10.0, 12.0, 15.0, 2.0, 24.0, 30.0, 36.0, or 48.0 hours, preferably from about 0.5 to about 2 hours.

Optionally, the first impregnated support is then subjected to a drying step at a temperature of less than about 200° C., for example, from about 80 to about 200° C., or from about 100 to about 180° C. to remove the water or other solution carrier, and organic dispersant, if present, to obtain a first dried inorganic support. The first dried inorganic support may contain less than about 5.0, 4.5, 4.0, 3.0, 2.0, 1.5, or 1.0 wt % of water by weight of the first dried support. The drying step may be accomplished by any technique known to those skilled in the art that is effective for removal of the water or other solution carrier, for example exposure to heated air, vacuum drying at a pressure below atmospheric pressure, or microwave drying.

Often, the catalyst preparation methods of the present disclosure further comprise the steps of: c) providing a second solution containing cations of a second metal, wherein the second metal is selected from Groups 6-10 of the Periodic Table of Elements, preferably platinum and/or palladium; and d) impregnating the first impregnated inorganic support, or the first dried inorganic support if a drying step is included, with the second solution.

The second solution can be prepared by dissolving a source of the second metal, or a precursor thereof, in a solution carrier, e.g., water. Optionally, an organic dispersant may be added to assist in uniform application of the first metal component to the support. Suitable organic dispersants include amino alcohols and amino acids, such as arginine. For example, the organic dispersant may be present in the solution composition in an amount between 1.0 wt % and 20 wt % of the solution composition.

Preferably, the second metal comprises platinum and/or palladium. Generally, useful sources or precursors of the second metal are free or substantially free of halogen species, e.g., chlorine. Preferred sources or precursors of the second metal contain the first second in cationic form, e.g., nitrates, hydrides, hydroxides, or sulfides of the second metal.

Typically, the pH value of the second solution is greater than the IEP of the inorganic support. Preferably, the second solution has a pH value of greater than about 6.5, 7.0, 7.5, 8.0, 9.0, 10.0, 11.0, 12.0, or about 13.0. For example, preferred ranges of the pH value of the second solution can be from about 6.5 to about 14.0, e.g., from about 7.0 to about 14.0, or from about 8.0 to about 14.0.

The impregnation step of the first impregnated support, or the first dried inorganic support if a drying step is included, to obtain a second impregnated support can generally be conducted at a temperature of less than about 100° C., for example, from about 20 to about 25° C., for a time period of at least about 0.1, 0.2, 0.5, 0.8, 1.0, 1.5, 2.0, 3.0, 4.0, 5.0, 6.0, 7.0, 8.0, 10.0, 12.0, 15.0, 2.0, 24.0, 30.0, 36.0, or about 48.0 hours, preferably from about 0.5 to about 2 hours.

Optionally, the second impregnated support is then subjected to a drying step at a temperature of below about 200° C., for example, from about 80 to about 200° C., or from about 100 to about 180° C. to remove most solution carriers, and organic dispersant, if present, to obtain a second dried inorganic support. The second dried inorganic support may contain less than about 5.0, 4.5, 4.0, 3.0, 2.0, 1.5, or about 1.0 wt % of water by weight of the second dried support.

In any embodiment, the first, and optionally second, impregnated (optionally dried) inorganic support generally comprises a composition comprising (i) anions of a first metal, wherein the first metal is selected from Group 14 of the Periodic Table of Elements, preferably tin; and (ii) optionally, cations of a second metal, wherein the second metal is selected from Groups 6-10 of the Periodic Table of Elements, preferably palladium and/or palladium, wherein the anions of the first metal, and optionally the cations of the second metal, are deposited on a silica-containing support. Prior to being used in a dehydrogenation reaction, the resulting composition, i.e, the first or second impregnated inorganic support, is typically calcined in one or more stages, generally at a temperature of 100° C. to 700° C., preferably from about 250 to about 650° C., or from about 300 to about 600° C., for a time of 0.5 to 50 hours, to effect one or more of: (a) removal of the solution carrier; (b) conversion of a metal component, typically at least the first metal, to an oxide form; and (c) decomposition of the organic dispersant. The heating may be conducted in an oxidizing atmosphere, such as air. The calcined catalyst composition may comprise less than about 3.0, 2.0, 1.5, 1.0, 0.5, or about 0.1 wt % of water by weight of the dehydrogenation catalyst.

In any embodiment, the dehydrogenation catalyst may optionally further comprise a third metal selected from Group 1 and Group 2 of the Periodic Table of Elements. In such aspects, the optional Group 1 and/or Group 2 metal can be added in substantially the same manner as addition of the second metal described herein, i.e., via impregnation, of the (optionally dried) inorganic support with a third solution containing ions of the third metal.

In any embodiment, in the dehydrogenation catalyst prepared in accordance with the methods of the present disclosure, the metal selected from Group 14 is typically present in an amount in the range of between any two of the following percentages: about 0.01 wt %, about 0.03 wt %, about 0.05 wt %, about 0.08 wt %, about 0.10 wt %, about 0.15 wt %, about 0.30 wt %, about 0.50 wt %, about 0.80 wt %, about 1.00 wt %, about 1.50 wt %, about 2.00 wt %, about 2.50 wt %, about 3.00 wt %, about 3.50 wt %, about 4.00 wt %, about 4.50 wt %, about 5.00 wt %, about 5.50 wt %, about 6.00 wt %, about 6.50 wt %, about 7.00 wt %, about 7.50 wt %, about 8.00 wt %, about 8.50 wt %, about 9.00 wt %, about 9.50 wt %, and about 10.0 wt %, for example from about 0.01 wt % to about 10.00 wt %, or from about 0.05 wt % to about 5.00 wt % based on the weight of the dehydrogenation catalyst.

In any embodiment, in the dehydrogenation catalyst prepared in accordance with the methods of the present disclosure, the metal selected from Groups 6 to 10 is typically present in an amount in a range between any two of the following percentages: about 0.01 wt %, about 0.02 wt %, about 0.03 wt %, about 0.05 wt %, about 0.08 wt %, about 0.10 wt %, about 0.30 wt %, about 0.50 wt %, about 0.80 wt %, about 1.00 wt %, about 1.50 wt %, about 2.00 wt %, about 2.50 wt %, about 3.00 wt %, about 3.50 wt %, about 4.00 wt %, about 4.50 wt %, or about 5.00 wt %, about 5.50 wt %, about 6.00 wt %, about 6.50 wt %, about 7.00 wt %, about 7.50 wt %, about 8.00 wt %, about 8.50 wt %, about 9.00 wt %, about 9.50 wt %, and about 10.0 wt %, from example from about 0.01 wt % to about 10.00 wt %, or from about 0.10 wt % to about 5.00 wt % based on the weight of the dehydrogenation catalyst.

Alternatively or additionally, the dehydrogenation catalyst may comprise (i) nickel at a concentration of at most about 2.0 wt %, or at most about 1.0 wt %, or at most about 0.5 wt %, or at most about 0.1 wt %; and (ii) cobalt at a concentration of at most about 2.0 wt %, or at most 1.0 wt %, or at most about 0.5 wt %, or at most 0.1 about wt %, the percentages based on the weight of the dehydrogenation catalyst. Preferably, the catalyst composition is free or substantially free of ruthenium, rhodium, lead, and/or germanium, and/or any other active elemental components.

The ratio of the second metal selected from Groups 6 to 10 of the Periodic Table of Elements to the first metal selected from Group 14 of the Periodic Table of Elements (e.g., the Pt/Sn ratio) in the catalyst can be in a range between any two of the following values: about 0.1, about 0.2, about 0.3, about 0.4, about 0.5, about 0.8, about 1.0, about 2.0, about 2.5, about 3.0, about 4.0, about 5.0, about 8.0, about 10.0, about 15.0, about 20.0, about 30.0, about 40.0, about 50.0, about 60.0, about 70.0, about 80.0, about 90.0, about 100, about 150, about 200, about 250, about 300, about 350, and about 400, for example from about 2.5 to about 400; from about 2.5 to about 200; and from about 3.0 to about 100.

It will be understood that the first metal, second metal, and third metal may not be purely the elemental metal, but could, for example, be at least partly in another form, such as a salt, oxide, hydride, sulfide, carbonate, etc., even though the composition of the catalyst is expressed in terms of elemental metals for the first, second, and third metals. For example, where the catalyst is prepared by a step of calcination in air or other $O_2$-containing atmosphere, at least a part of the metal(s) are in an oxidized form. For example, if the catalyst comprises Pt and Sn and a silica support, the catalyst would typically comprise at least a part of Pt in the form of $PtO_2$, and a part of Sn in the form of $SnO_2$.

In any embodiment, the dehydrogenation catalyst prepared in accordance with the methods of the present disclosure is generally free or substantially free of halogen species.

In any embodiment, the dehydrogenation catalyst may be subjected to a step of activation prior to being used in a dehydrogenation reaction. The activation step typically involves heating the catalyst in a reducing atmosphere comprising $H_2$ at an elevated temperature. The reducing atmosphere can be pure hydrogen, or a mixture of hydrogen with other reducing or inert gas, such as $N_2$, $CH_4$, $C_2H_5$, other hydrocarbons, and the like. Preferably, the $H_2$-containing atmosphere used for the activation step prior to contacting the catalyst is a substantially dry stream of gas comprising $H_2O$ at no more than about 5.0, 4.0, 3.0, 2.0, 1.0, 0.8, 0.5, 0.3, 0.1, 0.05, 0.01, 0.005, 0.001, 0.0005, or even about 0.0001 vol %. The dry $H_2$ stream can serve to heat the catalyst precursor, dry the precursor before significant reduction occurs, and purging the $H_2O$ produced during reduction, if any. Upon contacting with hydrogen at high temperature, the first metal, if in an oxidation state higher than elemental, would typically be at least partly reduced to a lower oxidation state, advantageously elemental state. The second metal, if in an oxidation state higher than elemental, may be reduced to a lower oxidation state or elemental state as well in the activation step by hydrogen and/or other components in the activation atmosphere. For example, $PtO_2$ and PdO can be reduced to Pt and Pd by $H_2$ at an elevated temperature. The third metal, however, being a Group 1 or 2 metal in the Periodic Table such as K, Na, Ca, and the like, if present in the catalyst, would most likely remain in an oxidation state higher than elemental in the activated catalyst in the form of oxide, salt, or part of complex material such as a glass or ceramic material formed with the inorganic support material.

During the activation step, the catalyst may be heated from a lower temperature, e.g., room temperature, to a target activation temperature. As used herein, "activation temperature" means the highest temperature the catalyst is exposed to for at least 3 minutes (or at least 5 minutes, or at least 10 minutes, or at least 15 minutes, or at least 20 minutes) during activation. It is highly desired that the catalyst is surrounded by a $H_2$-containing atmosphere during the heating step. When the temperature is relatively low, e.g., lower than 100° C., reducing of the first and/or second and/or third metal(s) can be slow and negligible. The higher the temperature of the catalyst precursor, the higher the rate of the reducing reactions. Thus, it is desired that the highest temperature the catalyst is exposed to (and thus, reached) during the activation step is not lower than about 300, 320, 340, 350, 360, 380, 400, 420, 440, or 450° C.

In any embodiment the catalyst is held within the temperature range from $T_{act}$-20° C. to $T_{act}$ for an activation duration of at least D1 minutes, where $T_{act}$ is the activation temperature, and D1 can be about 10, 15, 20, 25, 30, 45, 60, 75, 90, 120, 150, 180, 240, 300, 360, 420, 480, 540, 600, 660, 720, 780, 840, or even 900. It has been found that too high an activation temperature and too long a temperature hold period around the maximal temperature can be detrimental to the performance of the activated catalyst. Without intending to be bound by a particular theory, it is believed that the first and second metals in elemental form may be mobilized on the surface of the inorganic support at very high temperature, agglomerate to form large crystals, thereby reducing the number of effective sites on the activated catalyst. Thus, it is desired that the activation temperature the catalyst is exposed to in the activation step is not higher than about 650, 640, 630, 620, 610, 600, 590, 580, 570, 560, or 550° C. It is desired that during the heating step and the temperature hold period, the catalyst is exposed to a $H_2$-containing atmosphere at least b % of the time, where b can be about 50, 60, 70, 80, 90, 95, 98, or even 100%. When and if the catalyst is not surrounded by an $H_2$-containing atmosphere, it is highly desired that it is surrounded by an otherwise reducing or inert atmosphere, such as $CH_4$, $N_2$, and mixtures thereof, and the like.

At the end of the temperature holding period around the activation temperature, it is desired that at least about 40%, 50%, 55%, 60%, 65%, 70%, 75%, 80%, 85%, 90%, 95%, 98%, 99%, 99.5%, 99.8%, or even 99.9% of all of the first and second metals in the catalyst have been reduced to the desired oxidation state, such as elemental state. Where the catalyst comprises Pt and/or Pd, it is desired that at least about 50%, 55%, 60%, 65%, 70%, 75%, 80%, 85%, 90%, 95%, 98%, 99.5% or even 99.8% of Pt and/or Pd are reduced to elemental Pt and Pd at the end of the temperature holding period. Where the catalyst comprises Sn, it is desired that at least about 40%, 45%, 50%, 55%, 60%, 65%, 70%, 75%, 80%, 85%, 90%, 95%, 98%, or even 99% of Sn is reduced to elemental Sn at the end of the temperature holding period.

The activated dehydrogenation catalyst typically has a hydrogen chemisorption value (hcv) of greater than about 0.05, 0.08, 0.12, 0.15, 0.18, 0.20, 0.25, 0.30, 0.50 or about 0.70.

Preferably, the Alpha Value of the dehydrogenation catalyst is from about 0 to about 10, such as from about 0 to about 5, or from about 0 to about 1. The Alpha Value of the support is an approximate indication of the catalytic cracking activity of the catalyst compared to a standard catalyst.

As used herein, the "Alpha Value" of a molecular sieve catalyst is a measure of the cracking activity of that catalyst using n-hexane conversion at 538° C. in a Quartz plug flow reactor at atmospheric pressure. Catalytic cracking activity is typically indicated by the weight percent conversion of hexane to lower boiling C1 to C5 hydrocarbons. The experimental conditions of the test include sizing the catalyst to 14-25 mesh and diluting with quartz, and heating the catalyst to a constant temperature of 538° C. and exposure to the feed in the plug flow reactor. The feed consists of a mixture of n-hexane in helium, at a hexane partial pressure of 100 Torr (133 mbar). The WHSV is adjusted to keep the hexane conversion between 5 and 25%. Four data points are measured at 4 minutes, 11 minutes, 18 minutes, and 25 minutes time on stream. The reported Alpha value is taken after 18 min time of stream. The n-hexane cracking activity, expressed as Alpha, is defined as the first order rate constant for n-hexane conversion relative to a silica-alumina standard (amorphous aluminosilicate catalyst obtained by co-gellation, 10% alumina, surface area of 420 m²/g, no cations in base exchanging solution), and determined using formula: α=A·ln(1−X)/τ; where "α" is the relative first order rate constant, and:

"A" includes the reference rate constant and unit conversion=−1.043;
is "X" is the fractional conversion;
"τ" is the residence time=wt/(ρ·F);
"ρ" is the packing density in g/cm³;
"F" is the gas flow rate in cm³/min;
"wt" is the catalyst weight in g.

Alpha Values for some typical catalysts are: ZSM-5 with no cation exchange (38), and with H⁺ exchange (450); synthetic Faujasite exchanged in calcium ions (1.1), and exchanged in H(NH₄) (6,400).

Alternatively, the Alpha Value may range from valpha1 to valph2, where 'valpha1' can be 0.0, 0.1, 0.2, 0.3, 0.4, 0.5, 0.6, 0.7, 0.8, 0.9, 1, 2, 3, 4, 5, 6, 7, 8, 9, and 10; and 'valpha2' can be 200, 175, 150, 125, 100, 90, 80, 70, 60, 50, 40, 30, 20, 10, 5, 1.9, 1.8, 1.7, 1.6, 1.5, 1.4, 1.3, 1.2, 1.1, 1, 0.9, 0.8, 0.7, 0.6, and 0.5, as long as valpha1<valpha2.

Dehydrogenation Process

The activated dehydrogenation catalyst made by using the methods of the present disclosure can be used for dehydrogenating a first composition comprising any dehydrogenable hydrocarbon materials such as those containing a cyclic hydrocarbon compound. Preferably, the first composition comprises a cyclic hydrocarbon compound, such as cyclopropane, cyclobutane, cyclopentane, cyclohexane, cycloheptane, cyclooctane, cyclododecane, cyclodecane, cycloundecane, and derivatives (such as alkylated derivatives) thereof. The first composition may comprise C1 wt % to C2 wt % of a saturated cyclic hydrocarbon (e.g., cyclohexane), where C1 and C2 can be, independently, 0.1, 0.2, 0.3, 0.4, 0.5, 0.6, 0.7, 0.8, 0.9, 1.0, 3.0, 5.0, 8.0, 10.0, 15.0, 20.0, 25.0, 30.0, 35.0, 40.0, 45.0, 50.0, 55.0, 60.0, 70.0, 75.0, 80.0, 85.0, 90.0, 95.0, 98.0, as long as C1<C2, where the percentages are based on the total weight of the first composition contacting the activated catalyst.

Where the first composition comprises a six-membered cyclic hydrocarbon such as cyclohexane, it may further comprise one or more five-membered ring cyclic hydrocarbon (such as cyclopentane, methylcyclopentane, ethylcyclopentane, and the like), at a concentration based on the total weight of the first composition in a range from C3 wt % to C4 wt %, where C3 and C4 can be, independently, 0.01, 0.03, 0.05, 0.08, 0.10, 0.15, 0.20, 0.25, 0.30, 0.35, 0.40, 0.45, 0.50, 0.60, 0.70, 0.80, 0.90, 1.00, 1.50, 2.00, 2.50, 3.00, 3.50, 4.00, 4.50, 5.00, as long as C3<C4.

The first composition may further comprise a non-dehydrogenable component, such as an aromatic hydrocarbon, at a concentration based on the total weight of the first composition in a range from C5 wt % to C6 wt %, where C5 and C6 can be, independently, 5, 8, 10, 15, 20, 25, 30, 35, 40, 45, 50, 55, 60, 65, 70, 75, 80, 85, 90, or 95, as long as C1<C2. The aromatic hydrocarbon may be, for example, benzene. The aromatic hydrocarbon can be the same as the product of the dehydrogenation process using the activated dehydrogenation catalyst of the present disclosure. The non-dehydrogenable component in the first composition can serve as the heat carrier need for maintaining the dehydrogenation reaction at a desired temperature and reaction rate.

Suitable conditions for the dehydrogenation step include a temperature of about 100° C. to about 1000° C., a pressure of about 100 kPa-gauge to about 7000 kPa-gauge, e.g., atmospheric pressure, and a weight hourly space velocity of about 0.2 hr⁻¹ to about 50 hr⁻¹.

Preferably, the temperature of the dehydrogenation process can be from Td1° C. to Td2° C., where Td1 can be 100, 150, 200, 250, 300, 350, 400, 450, 500, 550, 600; and Td2 can be 1000, 950, 900, 850, 800, 750, 700, 650, 600, or 550, as long as Td1<Td2.

Preferably, the pressure of the dehydrogenation process can be from P1 kPa (gauge) to P2 kPa (gauge), where P1 and P2 can be, independently, 0, 100, 150, 200, 250, 300, 350, 400, 450, 500, 600, 700, 800, 900, 1000, 1500, 2000, 2500, 3000, 4000, 5000, 6000, or 7000 so long as the P1 is not higher than P2.

The reactor configuration used for the dehydrogenation process may comprise one or more fixed bed reactors containing a solid catalyst with a dehydrogenation function. Per-pass conversion of the saturated cyclic hydrocarbon (e.g., cyclohexane) using the present catalyst can be at least conv %, where cony can be 40, 50, 60, 70, 75, 80, 85, 90, 95, or even 98. The reaction is endothermic. Typically temperature of the reaction mixture drops across a catalyst bed because of the endothermic effect. External heat may be supplied through one or more heat exchangers to the reactant in the reactor to maintain the temperature of the reactant in the desired range. The temperature of the reaction composition drops across each catalyst bed, and then is raised by the heat exchangers. Preferably, 1 to 5 beds are used, with a temperature drop of 30° C. to 100° C. across each bed. Preferably, the last bed in the series runs at a higher exit temperature than the first bed in the series.

Although the present process can be used with any composition comprising a saturated cyclic hydrocarbon (e.g., cyclohexane) and, optionally a five-membered ring compound (e.g., methylcyclopentane), the process has particular application as part of an integrated process for the conversion of benzene to cyclohexanone and/or phenol. In such an integrated process the benzene is initially converted to cyclohexylbenzene by any conventional technique, including alkylation of benzene with cyclohexene in the presence of an acid catalyst, such as zeolite beta or an MCM-22 type molecular sieve, or by oxidative coupling of benzene to biphenyl followed by hydrogenation of the biphenyl. However, in practice, the cyclohexylbenzene is generally produced by contacting the benzene with hydrogen under hydroalkylation conditions in the presence of a hydroalkylation catalyst whereby the benzene undergoes the following reaction (1) to produce cyclohexylbenzene (CHB):

(1)

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are from 100° C. to 400° C., such as from 125° C. to 250° C., while suitable reaction pressures (gauge) are from 100 kPa to 7,000 kPa, such as from 500 kPa to 5,000 kPa. Suitable values for the molar ratio of hydrogen to benzene are between 0.15:1 and 15:1, such as between 0.4:1 and 4:1 for example, between 0.4:1 and 0.9:1.

The catalyst employed in the hydroalkylation reaction is generally a bifunctional catalyst comprising a molecular sieve of the MCM-22 type described above and a hydrogenation metal.

Any known hydrogenation metal can be employed in the hydroalkylation catalyst, although suitable metals include palladium, ruthenium, nickel, zinc, tin, and cobalt, with palladium being particularly advantageous. The amount of hydrogenation metal present in the catalyst can be in a range from 0.05 wt % to 10 wt %, such as from 0.1 wt % to 5.0 wt %, of the catalyst. Where the MCM-22 type molecular sieve is an aluminosilicate, the amount of hydrogenation metal present is such that the molar ratio of the aluminum in the molecular sieve to the hydrogenation metal is preferably from 1.5 to 1500, for example, from 75 to 750, such as from 100 to 300.

The hydrogenation metal may be directly supported on the MCM-22 type molecular sieve by, for example, impregnation or ion exchange. Preferably, at least 50 wt %, for example at least 75 wt %, and generally substantially all of the hydrogenation metal is supported on an inorganic oxide separate from, but composited with the molecular sieve. In particular, it is found that by supporting the hydrogenation metal on the inorganic oxide, the activity of the catalyst and its selectivity to desired products such as cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia.

The hydrogenation metal can be deposited on the inorganic oxide, such as by impregnation, before the metal-containing inorganic oxide is composited with the molecular sieve. Typically, the catalyst composite can be produced by co-pelletization, in which a mixture of the molecular sieve and the metal-containing inorganic oxide are formed into pellets at high pressure (generally 350 kPa to 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

The catalyst may comprise a binder. Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins, commonly known as Dixie, McNamee, Ga., and Florida clays or others in which the main mineral constituent is halloysite, kaolinite, dickite, nacrite, or anauxite. Such clays can be used in the raw state as originally mined or initially subjected to calcination, acid treatment, or chemical modification. Suitable metal oxide binders include silica, alumina, zirconia, titania, silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

Although the hydroalkylation step is highly selective towards cyclohexylbenzene, the effluent from the hydroalkylation reaction will normally contain unreacted benzene feed, some dialkylated products, and other by-products, particularly cyclohexane, and methylcyclopentane. In fact, typical selectivities to cyclohexane and methylcyclopentane in the hydroalkylation reaction are 1-25 wt % and 0.1-2.0 wt %, respectively.

The dehydrogenation reaction can be performed on all or a portion of the output of the hydroalkylation step.

Alternatively, the hydroalkylation reaction effluent is separated into at least a (i) $C_6$-rich composition; and (ii) the remainder of the hydroalkylation reaction effluent. When a composition is described as being "rich in" in a specified species (e.g., $C_6$-rich, benzene-rich or hydrogen-rich), it is meant that the wt % of the specified species in that composition is enriched relative to the feed composition (i.e., the input). A "$C_6$" species generally means any species containing 6 carbon atoms.

Given the similar boiling points of benzene, cyclohexane, and methylcyclopentane, it is difficult to separate these materials by distillation. Thus, a $C_6$-rich composition comprising benzene, cyclohexane, and methylcyclopentane may be separated by distillation from the hydroalkylation reaction effluent. This $C_6$-rich composition can be then subjected to the dehydrogenation process described above such that at least a portion of the cyclohexane in the composition is converted to benzene and at least a portion of the methylcyclopentane is converted to linear and/or branched paraffins, such as 2-methylpentane, 3-methylpentane, n-hexane, and other hydrocarbon components such as isohexane, C5 aliphatics, and $C_1$ to C4 aliphatics. The dehydrogenation product composition may then be fed to a further separation system, typically a further distillation tower, to divide the dehydrogenation product composition into a benzene-rich stream and a benzene-depleted stream. The benzene-rich stream can then be recycled to the hydroalkylation step, while the benzene-depleted stream can be used as a fuel for the process. When a composition is described as being "depleted" with respect to a particular species (e.g., benzene-depleted), it is meant that the wt % of the specified species in that composition is depleted relative to the feed composition (i.e., the material charged into the reactor).

After separation of the $C_6$-rich composition, the remainder of hydroalkylation reaction effluent may be fed to a second distillation tower to separate the monocyclohexylbenzene product (e.g., cyclohexylbenzene) from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Transalkylation with additional benzene may be effected in a transalkylation reactor, separate from the hydroalkylation reactor, over a suitable transalkylation catalyst, including large pore molecular sieves such as a molecular sieve of the MCM-22 type, zeolite beta, MCM-68 (see U.S. Pat. No. 6,014,018), zeolite Y, zeolite USY, and mordenite. A large pore molecular sieve may have an average pore size of at least 7 Å, such as from 7 Å to 12 Å. The transalkylation reaction is typically conducted under at least partial liquid phase conditions, which suitably include a temperature of 100° C. to 300° C., a pressure of 800 kPa to 3500 kPa, a weight hourly space velocity of 1 $hr^{-1}$ to 10 $hr^{-1}$ on total feed, and a benzene/dicyclohexylbenzene weight ratio of 1:1 to 5:1. The transalkylation reaction effluent can then be returned to the second distillation tower to recover the additional monocyclohexylbenzene product produced in the transalkylation reaction.

After separation in the second distillation tower, the cyclohexylbenzene can be converted into phenol and cyclohexanone by a process similar to the Hock process. In this process, cyclohexylbenzene is initially oxidized to the corresponding hydroperoxide. This is accomplished by introducing an oxygen-containing gas, such as air, into a liquid phase containing the cyclohexylbenzene. Unlike the Hock process, atmospheric air oxidation of cyclohexylbenzene, in the absence of a catalyst, is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide Preferably, the catalyst is N-hydroxyphthalimide. Another suitable catalyst is N,N',N"-trihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 wt % to 5.0 wt %, of the cyclohexylbenzene.

Suitable conditions for the oxidation step include a temperature between 70° C. and 200° C., such as 90° C. to 130° C., and a pressure of 50 kPa to 10,000 kPa. Any oxygen-containing gas, preferably air, can be used as the oxidizing agent. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

Another reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of 20° C. to 150° C., such as 40° C. to 120° C., and a gauge pressure of 50 kPa to 2,500 kPa, such as 100 kPa to 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction can be conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid, and p-toluenesulfonic acid. Ferric chloride, boron trifluoride, sulfur dioxide, and sulfur trioxide are also effective homogeneous cleavage catalysts. The preferred homogeneous cleavage catalyst is sulfuric acid, with preferred concentrations in the range of 0.05 wt % to 0.5 wt %. For a homogeneous acid catalyst, a neutralization step preferably follows the cleavage step. Such a neutralization step typically involves contact with a basic component, with subsequent removal of a salt-enriched phase by decanting or distillation.

A suitable heterogeneous catalyst for use in the cleavage of cyclohexylbenzene hydroperoxide includes a clay, such as an acidic montmorillonite silica-alumina clay, as described in U.S. Pat. No. 4,870,217, or a faujasite molecular sieve as described in WO 2012/145031.

The effluent from the cleavage reaction comprises phenol and cyclohexanone in substantially equimolar amounts and, depending on demand, the cyclohexanone can be sold or can be dehydrogenated into additional phenol. Any suitable dehydrogenation catalyst can be used in this reaction, such as the dehydrogenation catalyst or a variation of the catalyst described herein. Suitable conditions for the dehydrogenation step comprise a temperature of 250° C. to 500° C. and a pressure of 0.01 atm to 20 atm (1 kPa to 2030 kPa), such as a temperature of 300° C. to 450° C. and a pressure of 1 atm to 3 atm (100 kPa to 300 kPa).

The invention will now be more particularly described with reference to the following non-limiting examples and the accompanying drawings.

EXAMPLES

Test Method—Elemental Mapping

Elemental mapping was performed using the scanning electron microscope (SEM) functionality of a JEOL JXA-8530f electron probe microanalyzer (EPMA). General sample preparation for the mapping comprised embedding the catalyst extrudates in an epoxy resin which was then cured, sliced, and polished to generate a cross-section sample of the extrudates for analysis. The mapping was carried out using a 10 μm probe size, operated at 15 keV and 50 nA.

Test Method—Gas Chromatography

Gas chromatography (GC) was performed using an Agilent 7890 GC equipped with dual flame ionization detectors (FID) and both a DB-1 column (60 m×0.32 mm i.d.×5 μm film, Agilent J&W Scientific) and a DB-Wax column (60 m×0.25 mm i.d.×0.5 μm film, Agilent J&W Scientific). The following oven procedure was utilized:
initial temperature of 35° C., hold for 5 min;
heat at a ramp rate of 100° C./min to 80° C., hold for 9.5 min;
heat at a ramp rate of 10° C./min to 115° C., then at a rate of 25° C./min to 225° C., hold for 8.6 min.

In the following examples, dehydrogenation catalysts comprising Sn and Pt (and essentially free of a third meal) deposited on a $SiO_2$ inorganic support having an IEP manufacturer specification of 3±0.5, were prepared by the following steps:
Step 1: an extruded silica support pellet having a composition >93% $SiO_2$, a B.E.T surface area of >90 $m^2/g$ and no measurable acidity as determined by Temperature Programmed Ammonia Adsorption was impregnated with 0.15 wt % tin using a first aqueous solution containing a tin source to obtain a first impregnated support;

Step 2: the first impregnated support was microwave dried at a temperature below 200° C. to reduce the water content to a level less than 5 wt % to obtain a first dried support;
Step 3: the first dried support was impregnated with 1 wt % platinum using a second aqueous solution of tetraamine platinum hydroxide having a pH value of 13.1 to obtain a second impregnated support;
Step 4: the second impregnated support was microwave dried at a temperature below 200° C. to reduce the water content to a level less than 5 wt % to obtain a second dried support; and
Step 5: the second dried support was calcined at a temperature of 350° C. for 1 hour to obtain the prepared dehydrogenation catalyst.

In each of the following examples, the prepared dehydrogenation catalysts had a nominal composition of 0.15 wt % Sn and 1 wt % Pt deposited on the silica support. All platinum dispersion values in the following examples were obtained using the hydrogen chemisorption method described herein.

Comparative Example 1

In this example, the tin source used in Step (1) above was stannous chloride dihydrate ($SnCl_2.2H_2O$). The first aqueous solution of Step (1) was prepared by dissolving the stannous chloride dihydrate in water. The pH value of the prepared first aqueous solution was determined as 2.37. After the calcination of Step (5) above, the obtained dehydrogenation catalyst exhibited a measured platinum dispersion of 0.12 H/Pt, indicating poor dispersion.

Comparative Example 2

In this example, the tin source used in Step (1) above was potassium stannate trihydrate ($K_2SnO_3.3H_2O$ (or $K_2Sn(OH)_6$)). The first aqueous solution of Step (1) was prepared by dissolving the potassium stannate trihydrate in water. The pH value of the prepared first aqueous solution was determined as 11.0. After the calcination of Step (5) above, the obtained dehydrogenation catalyst particle exhibited a measured platinum dispersion of 0.73 H/Pt, indicating very good dispersion. However, analysis of the obtained dehydrogenation catalyst via elemental mapping showed the tin concentrated on the surface of the catalyst, with no tin observed at the center of the catalyst particle. These elemental mapping analysis results suggest that the anionic tin species from the tin source exhibited poor distribution over the negatively charged surface of the silica support, as anticipated given the high pH of the first solution.

Example 1

In this example, the dehydrogenation catalyst was prepared by the same procedure as outlined for Comparative Example 2, except that 3 molar equivalents of citric acid (3 moles citric acid per mole of Sn) were added to the first aqueous solution in Step (1) prior to impregnation of the silica support. The pH value of the first aqueous solution after addition of the citric acid was determined as 2.78. After the calcination of Step (5), the obtained dehydrogenation catalyst exhibited a measured platinum dispersion of 0.62 H/Pt. Analysis of the obtained dehydrogenation catalyst via elemental mapping showed the tin evenly distributed across the catalyst particle.

Example 2

In this example, the dehydrogenation catalyst was prepared by the same procedure as outlined for Comparative Example 2, except that 4 molar equivalents of citric acid (4 moles citric acid per mole of Sn) were added to the first aqueous solution in Step (1). The pH value of the first aqueous solution after addition of the citric acid was determined as 2.44. After the calcination of Step (5), the obtained dehydrogenation catalyst exhibited a measured platinum dispersion of 0.58 H/Pt. Analysis of the obtained dehydrogenation catalyst via elemental mapping showed the tin evenly distributed across the catalyst particle.

Example 3

In this example, the dehydrogenation catalyst was prepared by the same procedure as outlined for Comparative Example 2, except that 5 molar equivalents of citric acid (5 moles citric acid per mole of Sn) were added to the first aqueous solution in Step (1). The pH value of the first aqueous solution after addition of the citric acid was determined as 2.33. After the calcination of Step (5), the obtained dehydrogenation catalyst exhibited a measured platinum dispersion of 0.51 H/Pt. Analysis of the obtained dehydrogenation catalyst via elemental mapping showed the tin evenly distributed across the catalyst particle.

Example 4

In this example, the dehydrogenation catalyst was prepared by the same procedure as outlined for Comparative Example 2, except that 10 molar equivalents of citric acid (10 moles citric acid per mole of Sn) were added to the first aqueous solution in Step (1). The pH value of the first aqueous solution after addition of the citric acid was determined as 2.01. After the calcination of Step (5), the obtained dehydrogenation catalyst exhibited a measured platinum dispersion of 0.34 H/Pt. Analysis of the obtained dehydrogenation catalyst via elemental mapping using an electron microprobe showed the tin evenly distributed across the catalyst particle.

Figure 1:
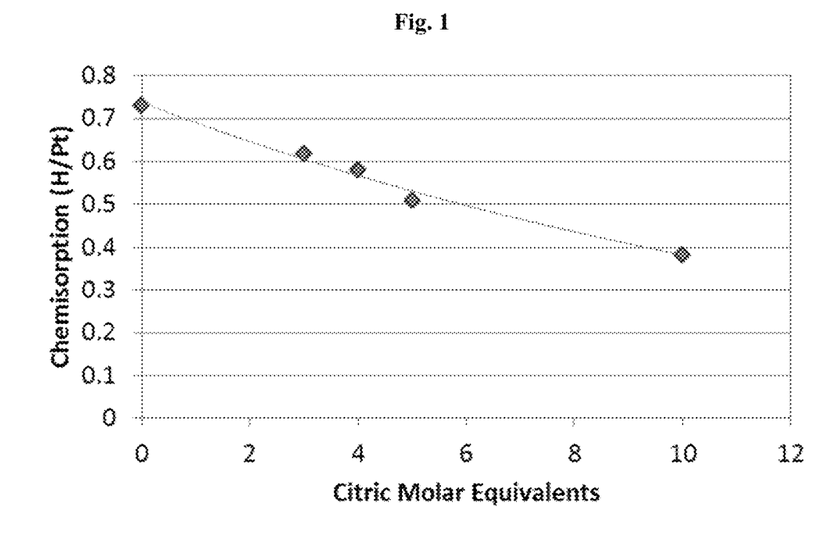
FIG. 1 graphically depicts the measured hydrogen chemisorption values, corresponding to Pt dispersion on the inorganic support surface, of the dehydrogenation catalyst particles prepared according to Comparative Example 2 and Examples 1 through 4.

FIG. 1 shows the dispersion of Pt in Comparative Example 2 and Examples 1 to 4. The results in FIG. 1 indicate that the dispersion and distribution of the Pt can be controlled by adjusting the pH of the first impregnation solution via the addition of a carboxylic acid, e.g., citric acid as used in Examples 1 through 4. As also seen in FIG. 1, Pt dispersion slowly decreases with increasing amounts of added citric acid. As such, FIG. 1 indicates that it is generally preferable to control the molar ratio of the carboxylic acid to the first metal, e.g., tin, to less than about 15 in order achieve acceptable dispersion of the second metal, e.g., Pt, such as at least about 0.2 H/Pt.

Example 5

Dehydrogenation Performance Tests with Comparative Example 2 and Examples at 1 Through 4

The dehydrogenation catalysts prepared in Comparative Example 2 and Examples 1 through 4 were tested for catalytic performance in the dehydrogenation of cyclohexane to benzene. The dehydrogenation experiments were conducted in a gas phase testing unit and carried out using dehydrogenation conditions comprising a temperature of 420° C., a pressure of 110 psig (760 kPa-g), a hydrocarbon WHSV of 10 $h^{-1}$, and a hydrogen to hydrocarbon molar ratio of 2. The dehydrogenation feed composition was nominally 89% benzene, 10% cyclohexane, and 1% methylcyclopentane. Gas exiting the reactor was analyzed via the gas chromatography procedure detailed above. Cyclohexane conversion, benzene selectivity, and catalyst deactivation rate were calculated via the below equations to evaluate the catalytic performance of the dehydrogenation catalysts:

Cyclohexane (CH) conversion (%)=(Moles of CH Fed−Moles of CH Produced)/Moles of CH Fed*100;

Benzene Selectivity (%)=Moles of Benzene Produced/(Moles of Benzene Produced+Moles of Other C6 and C12 Components Produced)*100, wherein Other C6 and C12 Components Produced includes species such as biphenyl, n-hexane, 2-methylpentane, and 3-methylpentane; and Deactivation Rate (%/day)=(CH conversion at −308 hours on stream−CH conversion at −246 hours on stream)/(308-246)*24 (hours/day).

Figure 2:
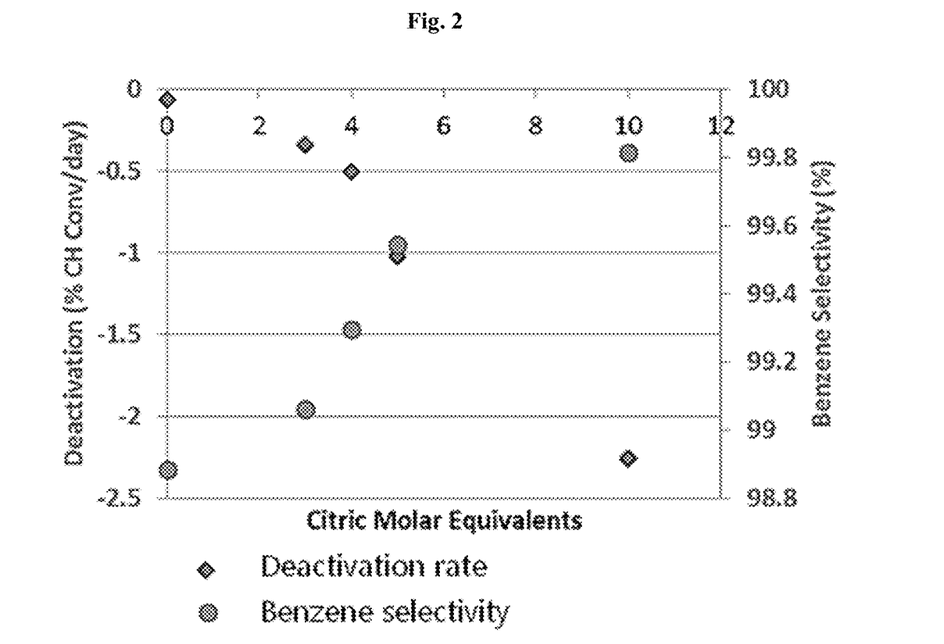
FIG. 2 graphically depicts the catalyst deactivation rate and benzene selectivity resulting from the performance evaluation tests conducted in Example 5 of the dehydrogenation catalysts prepared in Comparative Example 2 and Examples 1 through 4.

FIG. 2 shows the catalytic performance of the dehydrogenation catalysts prepared in Comparative Example 2, in which the pH of the first aqueous solution was not adjusted during catalyst preparation, and Examples 1 to 4, in which the pH of the first aqueous solution was adjusted by addition of citric acid during catalyst preparation.

As seen from FIG. 2, the catalytic performance of the tested dehydrogenation catalysts was strongly correlated with the metal dispersion, which can be controlled by adjusting the pH value of the first solution used in preparation of the synthesized catalysts (as shown in FIG. 1). Particularly, it can be seen from FIGS. 1 and 2 that as the amount of added citric acid is increased (i.e., as the pH value of the first solution is decreased), platinum dispersion decreases, leading to a desirable increase in benzene selectivity but accompanied by an undesired increase in the catalyst deactivation rate. Accordingly, it can be seen that one of ordinary skill in the art can adjust the pH value of the first solution to attain a desired catalyst performance.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. All documents described herein are incorporated by reference herein, including any priority documents and/or testing procedures to the extent they are not inconsistent with this text. Likewise, the term "comprising" is considered synonymous with the term "including" for purposes of Australian law and whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

The invention claimed is:

1. A method of preparing a dehydrogenation catalyst, the method comprising the steps of:
 a) providing a first solution, with a starting pH value higher than an isoelectric point of a silica-containing support to be impregnated, comprising anions of a first metal, wherein the first metal is selected from Group 14 of the Periodic Table of Elements, wherein the providing includes lowering a pH value of the first solution via addition of a carboxylic acid to cause the first solution to have a pH value of less than the isoelectric point of the silica-containing support; and
 b) impregnating the silica-containing support with the first solution to obtain a first impregnated silica-containing support,
 c) providing a second solution comprising cations of a second metal, wherein the second metal is selected from Groups 6-10 of the Periodic Table of Elements; and
 d) impregnating the first impregnated inorganic silica-containing support with the second solution, wherein the second solution has a pH value of greater than the isoelectric point of the silica-containing support.

2. The method of claim 1, wherein the pH value of the first solution is lowered to be in the range from about 1.0 to about 3.5.

3. The method of claim 1, wherein the first metal comprises tin.

4. The method of claim 1, wherein the first solution comprises stannate ions.

5. The method of claim 1, wherein the first solution is substantially free of halogen species.

6. The method of claim 1, wherein the carboxylic acid is selected from the group consisting of citric acid, acetic acid, oxalic acid, gluconic acid, glyoxylic acid, glycolic acid, lactic acid, valeric acid, adipic aid, and mixtures or combinations thereof.

7. The method of claim 1, wherein the carboxylic acid is added to the first solution in step a1) at a molar ratio of the carboxylic acid to the first metal in the range from about 1 to about 15.

8. The method of claim 1, wherein the silica-containing support comprises less than about 0.5 wt % alumina.

9. The method of claim 1, wherein the dehydrogenation catalyst comprises the first metal in an amount ranging from about 0.05 to about 5 wt % based on the weight of the dehydrogenation catalyst.

10. The method of claim 1 wherein the second solution has a pH value in the range from 8.0 to about 14.0.

11. The method of claim 1, wherein the second metal comprises platinum and/or palladium.

12. The method of claim 1, wherein the dehydrogenation catalyst comprises the second metal in an amount of from about 0.1 to about 10 wt % based on the weight of the dehydrogenation catalyst.

13. The method of claim 1, wherein the stannate includes potassium stannate.

14. The method of claim 1, wherein the first solution is substantially free of chlorine.

15. A method of preparing a dehydrogenation catalyst, the method comprising the steps of:
 a) impregnating a silica-containing support with a first aqueous solution of a stannate to obtain a first impregnated support;
 b) drying the first impregnated support at a temperature below about 200° C. to obtain a first dried support;
 c) impregnating the first dried support with a second aqueous solution containing cations of platinum and/or palladium to obtain a second impregnated support wherein the second solution has a pH value of greater than the isoelectric point of the silica-containing support;
 d) drying the second impregnated support at a temperature below about 200° C. to obtain a second dried support; and
 e) calcining the second dried support at a temperature of from about 100 to about 700° C.;
 wherein the first aqueous solution has a starting pH value higher than an isoelectric point of the silica-containing support and step a) includes lowering a pH value of the first aqueous solution to cause it to have a pH value below the isoelectric point of the silica-containing support via addition of a carboxylic acid selected from the group consisting of citric acid, acetic acid, oxalic acid, gluconic acid, glyoxylic acid, glycolic acid, lactic acid, valeric acid, adipic aid, and mixtures or combinations thereof.

16. The method of claim 15, wherein the first aqueous solution has a pH value in the range from about 1 to about 3.5.

17. The method of claim 15, wherein the dehydrogenation catalyst comprises from about 0.05 to about 5 wt % tin and from about 0.1 to about 10 wt % platinum based on the weight of the dehydrogenation catalyst.

18. The method of claim 15, wherein the silica-containing support comprises less than about 0.5 wt % alumina.

19. The method of claim 15, wherein the stannate includes potassium stannate.

* * * * *